United States Patent [19]
Chizick et al.

[11] Patent Number: 5,972,345
[45] Date of Patent: Oct. 26, 1999

[54] NATURAL PREPARATION FOR TREATMENT OF MALE PATTERN HAIR LOSS

[76] Inventors: Stephen Chizick; Rico Delorscio, both of 220 Duncan Mills Road, Suite 206, Toronto, Ontario, Canada, M3B 3J5

[21] Appl. No.: 09/303,675

[22] Filed: May 3, 1999

[51] Int. Cl.⁶ .......................... A61K 35/78; A61K 33/32; A61K 31/44
[52] U.S. Cl. ..................... 424/195.1; 424/342; 514/345
[58] Field of Search ................................. 424/195.1, 642; 514/345

[56] References Cited

U.S. PATENT DOCUMENTS

| | | | |
|---|---|---|---|
| 5,133,958 | 7/1992 | Stuckler | 424/61 |
| 5,407,675 | 4/1995 | Etemad-Moghadam | 424/74 |
| 5,422,100 | 6/1995 | Eliaz et al. | 424/70.11 |
| 5,750,108 | 5/1998 | Edwards | 424/195.1 |

*Primary Examiner*—Raymond Henley, III

[57] ABSTRACT

The present invention is directed to a natural formulation for treatment of male pattern hair loss. The formulation contains a combination of Saw Palmetto extract, African Pygeum extract, stinging nettle extract, and optionally zinc, vitamin B6 and green tea extract. The various extracts are prepared according to the traditional procedures, then combined in a suitable formulation for administration to the patient for treatment of the male pattern hair loss.

6 Claims, No Drawings

NATURAL PREPARATION FOR TREATMENT OF MALE PATTERN HAIR LOSS

FIELD OF THE INVENTION

The present invention is directed to a preparation for treatment of male pattern hair loss, and in particular, to a natural herbal and mineral preparation to help stop further hair loss and increase hair growth in a person having male pattern hair loss.

BACKGROUND OF THE INVENTION

Human hair undergoes a normal growth cycle where each hair grows continuously for approximately 2 to 4 years, and stops growing for 2 to 4 months, and then falls out. In its place, a new healthy hair begins to grow and this cycle is repeated. The hairs on the head are always in different stages of the cycle, so it is normal to loose scalp hair everyday. On average, up to about 100 hairs is lost per day.

In male pattern hair loss, the normal hair growth cycle is disrupted and more than the average number of hairs are shed per day without having the old hairs replaced by new ones. Male pattern hair loss is determined by a combination of male hormones (androgens) and heredity. Men susceptible to male pattern baldness usually experience the onset sometime in their 20's and it becomes more common as they age. Androgenetic alopecia is the most common type of hair loss in men, with approximately 50% of men experiencing this hair loss to some degree by the age of 50.

In addition to adrogenetic alopecia, other factors may influence hair loss, many of which are temporary. Amongst these factors include stress of an illness or major surgery, medicines, such as those used in chemotherapy, blood thinners, antidepressants, excessive amounts of vitamin A and certain disease states like diabetes.

There is increasing evidence of the link between male pattern hair loss and the level of 5 alpha-reductase. 5 alpha-reductase converts the hormone testosterone into dihydrotestosterone (DHT). There have been many reports of men with male pattern hair loss having increased levels of DHT in the scalp. It appears that DHT contributes to the shortening of the growth phase and thinning of the hair.

A number of preparations have recently been proposed for treating male pattern hair loss, of which the most well known is Minoxidil. Minoxidil is applied topically to the scalp and has been shown to stimulate hair growth in individuals with androgenetic alopecia. The exact mechanism of the action of Minoxidil in the treatment is not know, and it is thought that there is more than one mechanism by which Minoxidil stimulates hair growth. Some of the mechanisms by which Minoxidil may stimulate hair growth include phasodilation of the micro circulation around the hair follicles, which may stimulate hair growth; direct stimulation of the hair follicle cells to enter into a peripheral phase whereby resting phase follicles are stimulated to pass into active phase folicles; or alteration of the effect of androgens on genetically predetermined hair follicles. It was thought that Minoxidil might affect the androgen metabolism in the scalp, inhibiting the capacity of androgens to affect the hair follicles. Another medication utilized for treatment of adrogenetic alopecia is Finisteride. Finisteride is an inhibitor of type II 5-alpha-reductase and has been shown to be effective in decreasing scalp DHT by inhibiting conversion of testosterone to DHT. Oral administration of Finisteride slowed hair loss, increased hair growth and improved the appearance of hair.

5-alpha-reductase enzyme has also been linked to benign prostatic hyperplasia. A number of the medications now utilized for treating the male pattern hair loss were originally developed for treatment of benign prostatic hyperplasia.

Recently, there has been increased interest in the use of natural therapy for treatment of a diseased state. A number of herbal extracts have been demonstrated to be useful in the treatment of benign prostatic hyperplasia. Once such herbal extract is the extract of the berries of Saw Palmetto. Saw Palmetto is a small palm tree with large leaves and large deep red black berries. Saw Palmetto berries contain an oil with a variety of fatty acids and phytosterols. The fat soluble extract of Saw Palmetto berries has been shown to inhibit the conversion of testosterone, which is thought to be responsible for the enlargement of the prostrate. In addition, Saw Palmetto extract inhibits the binding of DHT to receptors, thus blocking DHT's action and promoting the breakdown of the potent compound. Another herbal extract utilized is African Pygeum. Pygeum is a large evergreen tree growing in the higher plateaus of southern Africa. The bark of the tree is processed to produce a fat-soluble fraction, which contains phytosterols, pentacyclic triterpenoids and ferulics esters of long chain fatty acids. African Pygeum extracts in double blind clinical trials have been found to be effective in treating a wide range of prostatic hyperplasia. Consumption of Pygeum extract resulted in a significant amelioration of symptoms, reduction in prostate size and clearance of bladder neck urethral obstruction.

Stinging nettles extract, which are an extract of a perennial plant growing worldwide, have been demonstrated to show a reduction in prostatic growth potential in mice with the administration of a high dosage of the nettle root extract. Stinging nettles have also been traditionally been known as a hair and skin tonic, stimulating hair growth, improving condition of the hair and skin and treating dandruff.

There still remains a need for a natural hair growth stimulant for use in treating androgenetic alopecia, having reduced side effects and risk of toxicity compared with synthesized pharmaceutical compounds.

SUMMARY OF THE INVENTION

In one aspect, the present invention provides for a composition for treating male pattern hair loss. The composition comprises Saw Palmetto extract, African Pygeum extract, stinging nettle extract, and optionally minerals, vitamins and other natural extracts.

In an aspect of the invention, the optional minerals, vitamins and other extracts include zinc salts, vitamin B6 and green tea extract.

DETAILED DESCRIPTION OF THE PREFERRED EMBODIMENTS

The present invention is directed to a natural formulation for treatment of male pattern hair loss. The formulation contains a combination of Saw Palmetto extract, African Pygeum extract, stinging nettle extract. The various extracts are prepared according to the traditional procedures, then combined in a suitable formulation for administration to the patient for treatment of the male pattern hair loss.

The Saw Palmetto extract is a extract of the berries of the Saw Palmetto tree, which is a small palm tree with large leaves and large deep red black berries. The Saw Palmetto extract is a purified fat-soluble extract prepared by extracting the fat-soluble components of the berries. These components include steroidal saponins, fatty acids, phytosterols, volatile oil, resins and tannins. The Saw Palmetto berries contain an oil with a variety of fatty acids and phytosterols. The fatty acids include capric, caprylic, caproic, lauric, palmitic and oleic acid and ethyl esters. The major phytosterols found in Saw Palmetto berries include beta-sitosterol, stigmasteriol, cycloartenol, lupcol, lupenone and 24-methyl-cycloartenol.

The African Pygeum extract is an extract of the air-dried bark from the trunk of the *Pygeum africanum*. *Pygeum africanum* is a large evergreen tree growing in the higher plateaus of southern Africa. The bark is collected and powdered, passed through a screen and extracted with chloroform to isolate the fat-soluble fractions. The lipophilic extracts are filtered and concentrated to dryness under vacuum until complete elimination of the chlorinated solvent. The African Pygeum extract contains three groups of active compounds. Phytosterols, such as beta-sitosterol, pentacyclic triterpenoids, such as ursolic and oleanic acids and ferulic esters of fatty alcohols, particularly the ferulic esters of docosanol and tetracosanol.

The stinging nettle extract are prepared from the young top leaves of stinging nettle plants. The top leaves are harvested from plants grown in clean, uncontaminated areas. The leaves are dried and powdered, then extracted with water and alcohol. The extract is concentrated to a paste and spray dried to produce a stable pure powder. The stinging nettle extract contains formic acid, histamine, acetylcholine, 5-hydroxy tryptamine, glucoquinones, minerals (including iron, magnesium, silica, potassium, sulfur), vitamins A, C, B2 and B5 and chlorophyll.

In addition to the above extracts, the formulation of the present invention may also include minerals, vitamins, or other natural extracts. Preferably, the optional minerals, vitamins and other extracts include zinc, vitamin B6 and green tea extract.

The zinc is preferably provided as a zinc salt, such as zinc acetate, zinc gluconate, zinc oxide or zinc sterate. Most preferably the zinc salt is the salt sold under the trademark OPTIZINC.

The optional vitamins used in the formulations may be any of the commonly used vitamins. Preferably, the vitamin, most preferably vitamin B6.

The green tea extract is a typical extract prepared from green tea leaves.

The formulations of the present invention may be provided in any form, which will be suitable for administration to the patient. While the formulation may be provided as a topical formulation for direct application to the scalp, it is preferred if the formulation is provided in a form suitable for oral administration to the patient. Thus, the formulation may be provided as preferably, the solid formulations or tablets or capsules, most preferably capsules. The oral formulations may be in the form of a liquid or solid formulation. Liquid formulations may include syrups, teas, etc., while the solid formulations may include powders, tablets and capsules.

The amount of each of the individual components present in the formulation is selective for optimum therapeutic effect. Preferably, the formulation contains the following amounts of the active ingredients:

| | |
|---|---|
| Saw Palmetto extract | 100–320 mg |
| Pygeum Africanum Extract | 25–100 mg |
| Urtica Dioica Extract | 50–200 mg |

-continued

| | |
|---|---|
| Zinc | 5–15 mg |
| Vitamin B6 | 25–75 mg |
| Green Tea Extract | 50–200 mg |

More preferably, the formulation contains:

| | |
|---|---|
| Saw Palmetto extract | 125–200 mg |
| Pygeum Africanum Extract | 40–75 mg |
| Urtica Dioica Extract | 75–150 mg |
| Zinc | 7–12 mg |
| Vitamin B6 | 40–60 mg |
| Green Tea Extract | 75–140 mg |

Most preferably, the formulation contains:

| | |
|---|---|
| Saw Palmetto Extract | 160 mg |
| Pygeum Africanum Extract | 50 mg |
| Urtica Dioica Extract | 120 mg |
| Zinc | 10 mg |
| Vitamin B6 | 50 mg |
| Green Tea Extract | 105 mg |

As noted above, the formulations for oral administration may be in the form of tablets or capsules. For tabletting, the active ingredients may be combined with typical excipients utilized in preparing tablets, such as binders and other tabletting agents. If prepared as capsules, the combined powdered ingredients will be filled into standard gelatin capsules and sealed.

The usual daily dose of the formulation of the present invention will comprise between:

| | |
|---|---|
| 200–500 mg | Saw Palmetto Extract |
| 50–200 mg | Pygeum Africanum Extract |
| 100–400 mg | Urtica Dioica Extract |
| 10–30 mg | Zinc |
| 50–150 mg | Vitamin B6 |
| 100–400 mg | Green Tea Extract |

More preferably, the usual daily dosage will comprise:

| | |
|---|---|
| 250–400 mg | Saw Palmetto Extract |
| 80–150 mg | Pygeum Africanum Extract |
| 150–300 mg | Urtica Dioica Extract |
| 15–25 mg | Zinc |
| 80–120 mg | Vitamin B6 |
| 150–280 mg | Green Tea Extract |

For most treatment, the optimum daily dosage is:

| | |
|---|---|
| 320 mg | Saw Palmetto Extract |
| 100 mg | Pygeum Africanum Extract |
| 240 mg | Urtica Dioica Extract |
| 20 mg | Zinc |
| 100 mg | Vitamin B6 |
| 210 mg | Green Tea Extract |

This dosage is ideally administered by administering two capsules, each containing the preferred formulation as set out above.

The formulations of the present invention are thought to affect male pattern hair loss through interaction with the production of dihydrotestosterone in the scalp. It is thought that the formulations of the present invention lock 5-alpha-reductase, the enzyme involved in the production of dihydrotestosterone from testosterone. Through this blockage of the 5-alpha-reductase, the level of dihydrotestosterone in the scalp is decreased, leading to the normalization of the hair growth cycle and the reversal of hair loss process normally associated with male pattern hair loss. The effects of the formulations of the present invention may not be immediately apparent. The formulation must be taken regularly in order to obtain maximum benefit.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. A natural formulation for treatment of male pattern hair loss, the formulation comprising a combination of Saw Palmetto extract, African Pygeum extract, and stinging nettle extract.

2. A formulation according to claim 1 wherein the formulation further comprises one or more other ingredients selected from natural herbal extracts, minerals and vitamins.

3. A formulation according to claim 2 wherein the one or more other ingredients are green tea extract, zinc salt and vitamin B6.

4. A formulation according to claim 3 wherein the formulation comprises:

| | |
|---|---|
| Saw Palmetto extract | 100–320 mg |
| Pygeum Africanum Extract | 25–100 mg |
| Urtica Dioica Extract | 50–200 mg |
| Zinc | 5–15 mg |
| Vitamin B6 | 25–75 mg |
| Green Tea Extract | 50–200 mg |

5. A formulation according to claim 4 wherein the formulation comprises:

| | |
|---|---|
| Saw Palmetto extract | 125–200 mg |
| Pygeum Africanun Extract | 40–75 mg |
| Urtica Dioica Extract | 75–150 mg |
| Zinc | 7–12 mg |
| Vitamin B6 | 40–60 mg |
| Green Tea Extract | 75–140 mg |

6. A formulation according to claim 5 wherein the formulation comprises:

| | |
|---|---|
| Saw Palmetto extract | 160 mg |
| Pygeum Africanum Extract | 50 mg |
| Urtica Dioica Extract | 120 mg |
| Zinc | 10 mg |
| Vitamin B6 | 50 mg |
| Green Tea Extract | 105 mg |

* * * * *